United States Patent [19]

Patel et al.

[11] Patent Number: 4,956,383

[45] Date of Patent: Sep. 11, 1990

[54] ANTIFUNGAL TRIACETYLENIC DIOXOLONE FROM *MICROBISPORA SP.* SCC 1438, ATCC 53620

[75] Inventors: Mahesh G. Patel, Verona; Ann C. Horan, Summit; Joseph A. Marquez, Montclair, all of N.J.; J. Allan Waitz, Portola Valley, Calif.

[73] Assignee: Schering Corporation, Kenilworth, N.J.

[21] Appl. No.: 89,278

[22] Filed: Aug. 25, 1987

[51] Int. Cl.$^5$ .................. A61K 31/365; C07D 317/36; C07D 317/38

[52] U.S. Cl. .................................. 514/467; 435/126; 549/229

[58] Field of Search ........................ 549/229; 514/467; 435/126

[56] References Cited

U.S. PATENT DOCUMENTS 4,806,565 2/1989 Hensens et al. ..................... 514/467

*Primary Examiner*—Richard L. Raymond
*Attorney, Agent, or Firm*—Thomas D. Hoffman; Gerald S. Rosen

[57] ABSTRACT

The novel triacetylenic dioxolone antifungal compound of this invention is isolated from the EV-22 complex of this invention which is elaborated by the microorganism *Microbispora sp.* SCC 1438, ATCC 53620.

12 Claims, No Drawings

ANTIFUNGAL TRIACETYLENIC DIOXOLONE FROM *MICROBISPORA SP.* SCC 1438, ATCC 53620

BACKGROUND OF THE INVENTION

This invention relates to a novel antifungal triacetylenic dioxolone isolated from an antifungal/antibiotic complex designated as EV-22. The compound is elaborated by the microorganism Microbispora sp. SCC 1438, ATCC 53620.

Naturally occurring antifungal acetylenic compounds are disclosed in *CRC Handbook of Antibiotic Compounds*, Vol. VI, 1978, pp. 360–376 and in *List of Fungal Products*, S. Shibata et al., C.C. Thomas Publishers, Springfield, IL, 1964. However, the triacetylenic dioxolone compounds and derivatives of this invention are not disclosed.

SUMMARY OF THE INVENTION

The present invention embraces Microbispora sp. SCC 1438, ATCC 53620 and mutants and variants thereof having the identifying characteristics of Microbispora sp. SCC 1438, ATCC 53620.

Another aspect the present invention is directed to the EV-22 complex produced by cultivating a strain of Microbispora sp. SCC 1438 having the identifying characteristic of ATCC 53620 in a pH and temperature controlled aqueous nutrient medium having assimilable sources of carbon and nitrogen under controlled submerged aerobic conditions until a composition of matter having substantial antifungal and antibiotic activity is produced.

The present invention is also directed to a compound represented by the formula I:

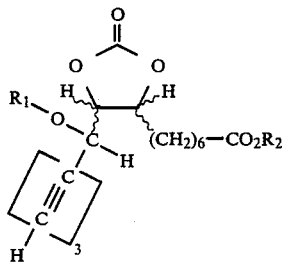

wherein $R_1$ is hydrogen or $(C_2-C_8)$alkanoyl, $R_2$ is hydrogen, lower alkyl or a pharmaceutically acceptable cation in racemic or optically active form. The compound of formula I wherein $R_1=R_2=H$ is a component of the EV-22 complex.

The present invention is also directed to an antifungal composition comprising a pharmaceutically acceptable carrier and a antifungally effective amount of a composition of matter selected from EV-22 complex and a compound represented by formula I. The present invention further contemplates a method eliciting an antifungal effect in a mammal having a susceptible fungal infection which comprises administering to said mammal an antifungally effective amount of a compound of formula I, an antifungally composition comprising a pharmaceutically acceptable carrier and an antifungally effective amount of a compound of formula I.

DETAILED DESCRIPTION OF THE INVENTION

The term "lower alkyl" refers to straight and branched chain hydrocarbon groups of 1 to 6 carbon atoms, such as methyl, ethyl, n-, and iso-propyl, n-, sec- and tert-butyl, n-, sec-, iso-, tert- and neo-pentyl, n-, sec-, iso- and tert-hexyl.

The term "$(C_2-C_8)$alkanoyl" refers to straight and branched chain alkanoyl groups having 2 to 8 carbon atoms such as acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 3-methylheptanoyl, oxtanoyl, 2-ethylhexanoyl and the like. Acetyl is preferred.

The term "pharmaceutically acceptable cations" means Group Ia and IIa cations especially $Li^+$, $Na^+$, $K^+$, $Ca^{++}$, $Mg^{++}$ and $Sr^{++}$ as well as $NH_4^+$, mono-, di- and triloweralkylammonium.

FERMENTATION OF THE MICROORGANISM

The antibiotic complex of this invention is produced when the elaborating microorganism, Microbispora sp. SCC 1438, ATCC 53620 is grown in an aqueous nutrient medium under submerged aerobic conditions at a temperature of about 27° C. to 40° C., preferably at from 27° C. to 35° C., and at a pH of from about 6.5 to 8.0 with agitation until substantial antibiotic activity is imparted to the medium. Temperature studies indicate that the organism grows rapidly at about 30° C. Therefore, the fermentation is preferably conducted employing a single temperature pattern of 30° C. for a period of about 24 to 96 hours. The fermentation is generally conducted from about 3 to 7 days, preferably for about 4 days. To determine when peak antibiotic production has been reached, samples of the medium were assayed every 24 hours for antibiotic content by bioassay of the whole broth against *C. albicans Wisconsin* and *Staphylococcus aureus* ATCC 209P. The growth of the organism (packed cell volume), pH and dissolved oxygen levels were determined either intermittently or continuously.

As nutrient medium, there is employed any suitable medium containing a source of carbon, for example an assimilable carbohydrate, and a source of nitrogen, for example an assimilable nitrogenous or proteinaceous material.

The medium employed for the fermentation contained OM peptone X and soy peptone and soluble starch as the major sources of nitrogen and carbon. Under these conditions the microorganism produced the antibiotic complex of this invention containing at least 3 biologically active components as determined by bioautography against *C. albicans Wisconsin* of the complex after development of a thin layer chromatography plate in 2:2:1 (v/v/v) chlorofrom: methanol: pH 3.5 acetate buffer.

The foregoing media are exemplary of the nutrients utilized by *Microbispora sp.* SCC 1438 to produce the antifungal/antibiotic EV-22 complex of this invention. However, it is obvious to those skilled in the fermentation art that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from about 6.5 to 8.0, a pH of from about 6.5 to 7.5 being preferred. Prior to sterilization, the pH of the medium is usually adjusted to about 6.5 and prior to inoculation the pH is usually adjusted to about 7.0.

The fermentation was initiated by addition of the inoculum to the sterilized fermentation medium. Generally, inoculum volume is 5% of total medium volume. The inoculum is prepared by addition of a sample of the frozen whole broth to an appropriate medium. A particularly preferred medium comprises beef extract, 0.3%; tryptone, 0.5; dextrose, 0.1%; potato starch, 2.4%; yeast extract, 0.5%; and calcium carbonate, 0.2%. The pH of the inoculum medium is adjusted to 7.5 prior to sterilization. The inoculum stage of the fermentation usually requires from 24 to 120 hours with 1 to 2 days preferred and is generally conducted at about 30° C.

ISOLATION AND PURIFICATION OF THE ANTIFUNGAL/ANTIBIOTIC COMPLEX EV-22

The EV-22 complex of this invention is produced when the elaborating organism, Microbispora sp. having the identifying characteristics of SCC 1438, ATCC 53620 is grown in an appropriate nutrient medium.

The antifungal/antibiotic EV-22 complex of this invention may be isolated from the fermentation broth by solvent extraction, and gel filtration chromatography and employing the following procedure:
  (a) Adjust the pH of the whole broth to 2 and filter;
  (b) Extract the filtrate using two volumes of organic solvent (e.g. ethyl acetate) each time for each volume of broth;
  (c) Wash the combined the organic solvent extracts with water and remove the organic solvent by stripping at 30° C. to yield an oily residue;
  (d) Dissolve the residue in acetonitrile and filter off the insolubles;
  (e) Add hexane to the filtrate until a yellow-brown precipitate forms;
  (f) Collect the precipitate.

Using the above procedure, 75g of antibacterial/antifungal EV-22 complex of this invention were obtained from 200 L of fermentation broth.

SEPARATION OF THE COMPLEX EV-22

The EV-22 complex of this invention is made up of at least three biologically active components, one of which has been isolated and characterized as the novel triacetylenic dioxolone of this invention, formula I, wherein $R_1=R_2=H$.

The active antifungal triacetylenic dioxolone of this invention can be isolated from EV-22 complex of this invention (preferably as the more stable methyl ester $R_1=H$, $R_2=CH_3$) by gel filtration chromatography using, for example, a Sephadex LH-20 gel filtration column. The eluate ($CH_3CN$) from the column was monitored by determining the activity of each fraction against *C. albicans* Wisconsin. The desired active fractions were combined and treated with anhydrous methanol previously saturated with HCl gas to give the methyl ester which was subject to High Performance Liquid Chromatography (HPLC) using acetonitrile/water to give the methyl ester of formula I, $R_1=H$; $R_2=CH_3$.

The structures of the compounds of this invention were determined by analysis of physiochemical properties of the methyl ester ($R_1=H$, $R_2=CH_3$) as well as compounds produced by the chemical reactions of the methyl ester. Thus, methanolysis of the triacetylene dioxolone in anhydrous methanol saturated with hydrogen chloride gas gave the methyl ester. The methyl ester is acetylated to give the O-acetate methyl ester, which upon treatment with iodine produces the diiodo-compound. The methyl ester was hydrogenated over Pd on charcoal to give the saturated methyl ester. The dioxolone moiety in the saturated methyl ester is removed by treatment thereof with NaOH to give the methyl 8, 9, 10-trihydroxyhexadecanoate, which upon acetylation produces the saturated dioxolone methyl ester O-acetate.

The Microorganism

The microorganism used, according to the present invention for the production of antibiotic/ antifungal EV-22 complex is Microbispora sp. SCC 1438.

A culture of this microorganism has been deposited in the collection of the American Type Culture Collection (ATCC) in Rockville, Md. where it has been assigned accession number ATCC 53620. Should the deposited culture become lost, destroyed or non-viable during the longer of the thirty year period from the date the culture was deposited or the five year period after the last request for the deposited culture or the effective life of the patent which issues from this application, the culture will be replaced by applicants or assignee(s) of this application upon notice. Subcultures of Microbispora sp. SCC 1438, ATCC 53620 are available during the pendency of this application to the one determined by the Commissioner of Patents and Trademarks to be entitled thereto under 37 C.F.R. 1.14 and 35 U.S.C. 122 and will be available to the public without restriction once a patent based on this application is granted. Use of the microorganism is dependent on the U.S. Patent Laws.

The compounds of formula I and EV-22 complex exhibited great antifungal activity in vitro against a range of *C. albicans* and dermatophytes; EV-22 complex also exhibits antibiotic activity against gram positive bacteria.

TAXONOMY OF MICROBISPORA SP. SCC 1438, ATCC 53620

Source

Microbispora sp. SCC 1438, ATCC 52620 was isolated from a mixture of soils plated on dilute yeast-starch agar containing an antibiotic complex.

Cultural Characteristics of Microbispora sp. SCC 1438, ATCC 53620

Microbispora sp. has beige to tan (ecru) vegetative mycelial pigments and gray-white to pink aerial mycelia; upon prolonged incubation, the aerial mycelia turn gray-green. Faint yellow-brown diffusible pigment is formed. (Descriptive media of Shirling and Gottleib, International Journal of Syst. Bacteriol., Vol. 16, pp. 313–340, "Methods for Characterization of Streptomyces Species," 1966. Waksman, The Actinomycetes, Vol. 2, The Williams & Wilkins Co., Baltimore, MD, 1961.)

Morphological Characteristics of Microbispora sp. SCC 1438, ATCC 53620

Substrate mycelia are long, irregularly branched, and do not fragment into short elements or form spores.

Aerial mycelia branch monopodially. Spores are born in longitudinal pairs closely arranged along the aerial hyphae and the spores are eliptical.

Cell Chemistry: Whole cells of Microbispora sp. SCC 1438, ATCC 53620 contain meso-diaminopimelic acid and madurose.

Growth Temperature: Growth of the culture is found from 27 to 40° C., but the culture does not grow at 45° C. The microorganism is mesophilic.

Generic Identification: Based on morphology and cell chemistry, ATCC 52620 is identified as a mesophilic species of Microbispora.

Pharmaceutical Composition

This invention also contemplates antifungally effective pharmaceutical compositions comprising an antifungally effective amount of a composition of matter selected from EV-22 complex and a compound of formula I in admixture with a pharmaceutically acceptable, nontoxic carrier adapted for topical, oral or parenteral use. The preferred mode of administration is topical.

Topical dosage forms may be prepared according to procedures well known in the art, and may contain a variety of ingredients. The formulations for topical use include ointments, creams, lotions, powders, aerosols, vaginal tablets, pessaries and sprays. Of these, ointments, lotions and creams may contain water, oils, fats, waxes, polyesters, alcohols, or polyols, plus such other ingredients as fragrances, emulsifiers and preservatives. Powders are made by mixing the active ingredient with a readily available, inert, pulverous distributing agent, such as talcum, calcium carbonate, tricalcuim phosphate, or boric acid. Aqueous suspensions of the above powders may also be made. Solutions or emulsions may also be prepared using inert solvents which are preferably nonflammable, odorless, colorless and nontoxic, for example vegetable oils, isopropanol, dimethyl sulfoxide, hydrogenated naphthalenes, and alkylated naphthalenes. Similarly, aerosol or non-aerosol sprays may be prepared using solutions or suspensions in appropriate solvents, e.g., difluorodichloromethane for aerosols.

In the case of topical formulations, e.g., ointments, creams, lotions, powders, tablets, pessaries or sprays, the formulation will contain about 0.1 to 10 grams of a compound of formula I per 100 grams of carrier.

In general, the dosage of compounds of formula I administered to combat a given fungal infection is similar to the dosage requirements of the present commercial products miconazole, clotrimazole, and ketoconazole.

In general, the topical dosage range will be from about 0.1% to about 10% by weight of a particular pharmaceutical composition formulated in single or divided doses, with the preferred range being about 0.5% to about 4% and with the most preferred range being about 1% to about 2%.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously are usually in the form of a sterile solution, and may contain salts or glucose to make the solution isotonic.

It will be appreciated that the actual preferred dosages of the compounds of this invention or pharmaceutically acceptable salts thereof will vary according to the particular compound being used, the particular composition formulated, the mode of application and the particular situs, host and disease being treated. Many factors that modify the action of the drug will be taken into account by the attending clinician, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests. The following examples illustrate the invention:

EXAMPLE 1

Preparation of EV-22 Complex

A. Inoculum Preparation

1. Initial Stage. To a 300 mL Erlinmeger flask, add 70 mL of the following germination broth:

| Ingredient | Wgt % |
| --- | --- |
| Beef Extract | 0.3% |
| Tryptone | 0.5 |
| Yeast Extract | 0.5 |
| Dextrose | 0.1 |
| Potato Starch | 2.4 |
| Calcium Carbonate | 0.2 |
| Dow Corning Antifoam B | 0.1 v/v |
| Water | 100 mL |

Adjust the pH of the germination broth to 7.5. Sterilize the broth and after cooling add 3.0 mL of the frozen (−20° C.) producing strain. Incubate at 30° C. with continual agitation at 250 rpm for 72 hrs.

2. Second Stage. Transfer 25 mL of the first stage germination broth to a 2-liter Erlenmeyer flask containing 500 mL of the same germination medium which had been previously pH adjusted and sterilized. Incubate at 30° C. with continual agitation at 240 rpm for 48 hrs.

3. Third Stage. Transfer 25 mL of the second stage germination broth to a 2-liter Erlenmeyer flask and repeat procedure of the second stage.

4. Fourth Stage. Transfer 5 volume percent of the third inoculum stage to a 14-liter New Brunswick Scientific laboratory fermentor containing 10 liters of the above-listed germination broth. Incubate the broth at 32° C. for 48 hrs. at an air flow of 0.25 VVM with continued agitation at 200 rpm.

| Fermentation Medium | |
| --- | --- |
| Ingredient | Weight (g) |
| Soy Peptone[1] | 6.0 |
| OM Peptone X[2] | 2.0 |
| Dextrose | 5.0 |
| Soluble Starch | 20.0 |
| Calcium Carbonate | 2.0 |
| Dow Corning Antifoam B | 1.0 mL |
| Tap Water | 1000 mL |

[1] Available from Sheffield Products, PO Box 630, Norwich, NY 13813.
[2] Available from Amber Labs, 3456 North Buffum St., Milwaukee, Wisconsin 53212.

Sterilize OM peptone X and Dextrose in separate flasks and add each to rest of the above-listed ingredients. Adjust pH of fermentation medium to 6.5 and sterilize the medium. Cool and adjust pH of the medium to 6.9–7.1.

To a 150-liter fermentor containing 5 volume percent of the fourth inoculum stage of step A, add 100 mL of the above-listed sterilized fermentation medium at pH 6.9–7.1.

Incubate the so formed fermentation broth at 32° C. at an air flow of 0.25 VVM with continual agitation at 200 rpm for 48 hrs. Evaluate antibiotic production by disc assays of an aliquot of the fermentation broth against *Candida albicans Wisconsin* and *Staphylococcus aureus* ATCC 209p at pH 7. The optimum antibiotic-/antifungal levels were normally produced after 48 hours of fermentation; longer fermentation times resulted in lower antibiotic/antifungal activity.

C. Isolation

Adjust the pH of the whole broth of Step B to 2 and filter the insolubles. Extract the filtrate twice with two volumes of ethyl acetate for each volume of filtrate. Combine the ethyl acetate solutions, dry them over anhydrous sodium sulfate and remove the solvent at 30° to give an oily residue. Dissolve the dried residue in acetone and remove the biologically inactive oils. Add the acetone solution to petroleum ether to form a yellow brown precipitate. Filter and vacuum dry the precipitate to give antibiotic/antifungal complex EV-22.

Bioautography of complex EV-22 on silica gel thin layer plates in a $CH_2Cl_2:CH_3OH$ 9:1 (v/v) solvent system demonstrated that complex EV-22 consists of at least three biologically active components.

EXAMPLE 2

Separation of Complex EV-22 -Isolation of the antifungal triacetyleneic Dioxolone of Formula I During attempts at concentration of the ethyl acetate solution in Step C of Example 1, decomposition of the EV-22 complex occurred spontaneously at room temperature as the ethyl acetate solution was brought to dryness.

Separation of the EV-22 complex from 200L of fermentation broth was accomplished using a modification of the procedure of Step C of Example 1. The ethyl acetate solutions were washed with water, dried and concentrated at 30° C. to give an oily residue. The oily residue was dissolved in acetonitrile ($CH_3CN$) and the inactive insolubles were removed by filtration. Hexane was added to the $CH_3CN$ solution to form a yellow-brown precipitate. The precipitate was dissolved in acetonitrile and placed on a Sephadex LH-20 column and eluted with neat acetonitrile. Three components were obtained: EV-22 H1 (major), H2 and H3; no yellow inactive contaminants. Upon concentration of the solution to dryness, EV-22 H1 (formula I wherein $R_1=R_2=H$) spontaneously degraded and lost antifungal activity.

EXAMPLE 3

Preparation of the Methyl Ester (Formula I; $R_2=CH_3$, $R_1=H$)

To a 2L round bottom flask containing fractions from LH-20 column containing the triacetylene dioxolone of formula I of Example 2, 300 mL of methanol (previously saturated with HCl gas) was added. The so formed reaction mixture was heated at reflux for 15 min and then cooled. The insolubles formed on cooling were removed by filtration and the volume of the filtrate concentrated to 100 mL Chloroform (300 mL) was added to precipitate the salts which were removed by filtration. The organic filtrate was washed with two portions of saturated sodium carbonate and of water and then dried over magnesium sulfate. The solvent was removed to give 500 mg of crude product. The crude product was dissolved in $CH_3CN$ and purified by HPLC using a μ Bondapak C-18 column having 1 $CH_3CN$:1 $H_2O$ (v/v) as the mobile phase. The fractions containing the active component were extracted with chloroform and the combined organic layers were washed with water and dried over magnesium sulfate. The solvent was removed to give 380 mg of the title compound. IR(KBr)γmax ($cm^{-1}$): 1810 (dioxolone,

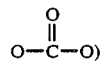

1755, 1725 (strong) and 2250 (v. weak); UV: $\lambda_{max}$ ($CH_3OH$): 255 270, 287 and 305 nm; $H^1$-NMR δ($CD_3CN$): 1.35–1.60 (10H,m,$CH_2$), 2.30 (2H,s,J=7.5 $CH_2CO$), 3.65 (3H,s,$OCH_3$) 2.20 (1H,s,≡CH) 4.3–4.7 (3H̄,m,$C_8HO$, $C_9HO$, $C_{10}HO$); $^{13}C$-NMR; δ$CD_3CN$) $C_2$–$C_7$: 24.7; 25.5; 29.5; 29.4, 34.5; 34.6;

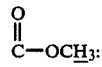

51.9; $C_8$, 63.0; $C_9$, 71.0; $C_{10}$, 79.3; $C_{16}$, 82.3;

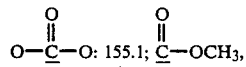

174.8 $C_{11}$–$C_{15}$ not observed. The methyl ester was hydrogenated in EtOAc over Pd/c catalyst to give the saturated methyl ester; MS (m/e)=344 ($M^+$) which corresponds to the molecular formula, $C_{18}H_{32}O_6$.

What is claimed is:

1. A compound represented by the formula I

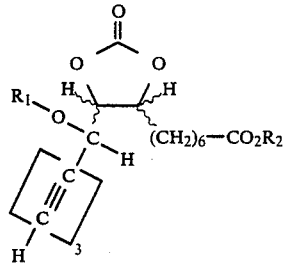

wherein $R_1$ is hydrogen or ($C_2$–$C_8$) alkanoyl and $R_2$ is hydrogen; lower alkyl or a pharmaceutically acceptable cation in racemic or optically active form.

2. A compound of claim 1 wherein $R_1$ and $R_2$ are hydrogen.

3. A compound of claim 1 wherein $R_1$ is $C_2$–$C_8$)alkanoyl.

4. A compound of claim 1 wherein $R_2$ is hydrogen.

5. A compound of claim 1 wherein $R_1$ is hydrogen.

6. A compound of claim 1 wherein $R_2$ is methyl.

7. A compound of claim 1 wherein $R_2$ is methyl and $R_1$ is hydrogen.

8. A compound of claim 1 wherein $R_1$ is acetyl.

9. A compound of claim 1 wherein $R_1$ is acetyl and $R_2$ is methyl.

10. An EV-22 complex produced by cultivating a strain of Microbispora sp. SCC 1438 having the identifying characteristics of ATCC 53620 in a pH and temperature controlled aqueous nutrient medium having assimilable sources of carbon and nitrogen under controlled submerged aerobic conditions until a composition of matter having substantial antifungal and antibacterial activity is produced.

11. An antifungal composition comprising a pharmaceutically acceptable carrier and a antifungally effective amount of a composition of matter selected from EV-22 complex of claim 10 and a compound represented by claim 1.

12. A method eliciting an antifungal effect in a mammal having a susceptible fungal infection which comprises administering to said mammal an antifungally effective amount of a compound of claim 1, or an antifungal composition comprising a pharmaceutically acceptable carrier and an antifungally effective amount of a compound of claim 1.

* * * * *